United States Patent
Nieuwenhuis et al.

(10) Patent No.: US 6,472,219 B1
(45) Date of Patent: Oct. 29, 2002

(54) USE OF TRACERS TO MONITOR APPLICATION OF TREATMENT PRODUCTS TO CUT FLOWERS

(75) Inventors: Heleen Nieuwenhuis, Leiden (NL); Jan A. M. Janssen, Almere (NL); John E. Hoots, St. Charles, IL (US)

(73) Assignee: Ondeo Nalco Company, Naperville, IL (US)

( * ) Notice: Subject to any disclaimer, the term of this patent is extended or adjusted under 35 U.S.C. 154(b) by 0 days.

(21) Appl. No.: 09/652,309

(22) Filed: Aug. 31, 2000

(51) Int. Cl.$^7$ .............................................. G01N 37/00
(52) U.S. Cl. ...................... 436/56; 422/82.08
(58) Field of Search .......................... 436/56; 422/82.08

(56) References Cited

U.S. PATENT DOCUMENTS

| | | | |
|---|---|---|---|
| 4,783,314 A | 11/1988 | Hoots et al. | 422/3 |
| 5,006,311 A | 4/1991 | Hoots et al. | 422/62 |
| 5,200,106 A | 4/1993 | Hoots et al. | 252/181 |
| 5,266,493 A | 11/1993 | Young | 436/55 |
| 5,817,600 A | 10/1998 | Carstairs et al. | 504/115 |
| 5,961,886 A | 10/1999 | Hasimoto et al. | 252/400 |

FOREIGN PATENT DOCUMENTS

| | | | |
|---|---|---|---|
| EP | 0 773 298 | 1/2000 | C12Q/1/06 |

OTHER PUBLICATIONS

The CAS REGISTRY web cite, http://www.cas.org/EO/regsys.html, printed Jun. 25, 2002, pp. 1–3.
Printout from American Chemical Society Registry Number Database, printed Jun. of 2002.
Brochure—Pokon & Chrysal—Naarden–Holland © 1999.

*Primary Examiner*—Jill Warden
*Assistant Examiner*—Monique T. Cole
(74) *Attorney, Agent, or Firm*—Margaret M. Brumm; Thomas M. Breininger

(57) ABSTRACT

A method to determine whether the desired amount of treatment product is present in water that cut flowers are placed in, is described and claimed. The method comprises formulating the treatment product so that it contains an inert fluorescent tracer, wherein the inert fluorescent tracer is added in a known proportion to the rest of the treatment product, then using a fluorometer to detect the fluorescent signal of the fluorescent tracer. The fluorescent signal of the fluorescent tracer is used to determine the amount of fluorescent tracer present and the amount of fluorescent tracer present is then used to determine the amount of treatment product present in the water that cut flowers are placed in. The amount of treatment product actually present in the water that cut flowers are placed in, is compared to the desired amount of treatment product that is supposed to be present in the water that cut flowers are placed in and optionally, the amount of treatment product added to the water that cut flowers are placed in is adjusted accordingly.

6 Claims, No Drawings

USE OF TRACERS TO MONITOR APPLICATION OF TREATMENT PRODUCTS TO CUT FLOWERS

FIELD OF THE INVENTION

This invention is in the field of products used for nutrition and care of plants and flowers. Specifically, this invention is in the field of monitoring the application of treatment products applied to cut flowers.

BACKGROUND OF THE INVENTION

The business of harvesting and supplying cut flowers from growing point to markets all over the world has created the need for treatment products that are applied to the water that the cut flowers are placed in. These treatment products prolong the life of the cut flowers and make it possible for the cut flowers to be shipped all over the world from their place of being grown to their final delivery point and arrive in saleable condition.

Cut flower treatment products are usually sold as concentrates and as such they are added to water in a certain concentration after which the cut flowers are placed in this mixture of water and product. Cut flower treatment products can also be sold as ready to use solutions.

The intended effects of the treatment products are many and varied. Some of the treatment products are designed to curtail ethylene production by the flowers, or reduce the sensitivity to ethylene of the flowers. Other treatment products are designed to decrease leaf yellowing and/or decrease microbial growth in the flower water and flower stem and/or decrease flower stem growth and/or stimulate water uptake. In addition, other treatment products can provide the flowers with nutrition for better development. The general flower quality, as measured by such criteria as vase life and/or leaf quality and/or flower quality, is improved by using these treatment products.

The cut flower treatment products can be used anywhere in the post-harvest chain of the flowers. Cut flower treatment products can be used by growers, auctions, bouquetmakers, supermarkets, florists and individual consumers. In the post-harvest chain of cut flowers several treatment products can be used consecutively, while combination of two or more products at one time is also possible. The duration of the treatment may vary from "quick dips" of about 10 seconds up to longer "transport treatments" which can last for many days. Many of the treatment programs are described as being short "pulse treatments" of about four hours.

In order to ensure that the cut flowers remain fresh and in saleable condition, it is important that the proper amount, usually referred to as "dosage" of treatment product is applied. Incorrect dosage can lead to serious problems. Overdosage may result in phytotoxicity symptoms in the cut flowers and consequently decrease instead of increase their vase life; moreover, the environment is exposed to more active ingredients than required in this case. In the case of underdosage, suboptimal results will be obtained as the flowers are exposed to an insufficient amount of active component(s). In the case of microbial growth, underdosage might even result in adverse effects as non anti-microbial ingredients in the products are then likely to stimulate microbial growth.

Dosage of the treatment products can be done by hand or by automation (i.e. dosing units). Dosages typically range from 0.05–3%, based on volume of treatment product and volume of cut flower water, but can also lie outside this range. Current practice includes checking the dosage based on measuring the level of an active component (i.e. aluminum sulfate, silver, amino-oxy-acetic acid) in the ready-to-use solutions and in samples thereof. In some cases instead of an active component a metal tracer (i.e. manganese) is being used for dosage control. Current methods of measuring these substances have one or more of the following problems: the analytical methods use bulky and costly equipment, interferences from other components present undermine the precision and accuracy of the analytical method, the methods are time-consuming, labor-intensive analyses that are not compatible with continuous monitoring and need to be carried out in a laboratory environment, and it is quite common for there to be degradation or deposition of active components resulting in inaccurate readings.

It would be desirable to have a simpler, less costly, more flexible analytical method that would enable the amount of treatment product present in said water that cut flowers are placed in to be measured.

SUMMARY OF THE INVENTION

This invention is a method to determine whether the desired amount of treatment product is present in water that cut flowers are placed in; comprising the steps of:
a) adding a known amount of an inert fluorescent tracer to a known amount of treatment product, with said treatment product being suitable for application to water that cut flowers are placed in;
b) applying said treatment product to water that cut flowers are placed in;
c) using a fluorometer to measure the fluorescent signal of said inert fluorescent tracer in said water that cut flowers are placed in; and optionally,
d) adjusting the amount of treatment product applied to said water that cut flowers are placed in, based on the measured fluorescent signal of said inert fluorescent tracer.

DETAILED DESCRIPTION OF THE INVENTION

Throughout this patent application the following terms have the indicated meanings:

"CAS Registry No." means the Chemical Abstracts Service Registry number;

"nm" stands for nanometers;

"Pokon" refers to Pokon & Chrysal BV, P.O. Box 5300, Gooimeer 7, 1410 AH Naarden, the Netherlands, telephone number 35 695-5888, fax number 35 695-5822.

"Chrysal SVB" means a treatment product applied to cut flowers in order to prevent leaf yellowing. It comprises gibberellin(s) or gibberellic acid(s). This product is available from Pokon.

"Chrysal RVB" means a treatment product applied to cut flowers in order to prevent vascular plugging of cut flower stems by bacteria. It comprises aluminum sulfate and biocides. This product is available from Pokon.

"Chrysal RVBn" means a treatment product applied to cut flowers in order to prevent vascular plugging of cut flower stems by bacteria. It comprises aluminum sulfate and surfactant. This product is available from Pokon.

"Chrysal OVB" means a treatment product applied to cut flowers in order to prevent vascular plugging of cut flower stems by bacteria. It comprises (a) quaternary ammonium compound(s). This product is available from Pokon.

"Chrysal EVB" means a treatment product applied to cut flowers in order to prevent ethylene damage. It comprises aminooxyacetic acid. This product is available from Pokon.

"Chrysal BVB" and "Chrysal BVB plus" means treatment products applied to cut flowers in order to prevent leaf yellowing, and/or extend vase life and/or reduce stem growth. These products comprise plant growth regulators like gibberellin(s) or gibberellic acid(s). These products are available from Pokon.

"Chrysal AVB" means a treatment product applied to cut flowers in order to prevent ethylene damage to cut flowers. This product comprises silver nitrate. This product is available from Pokon.

"Chrysal clear formulas (a whole range of formulas including Chrysal RVB clear and Chrysal clear professional products)" means treatment products applied to cut flowers to prevent vascular plugging of cut flower stems by bacteria and optionally formulated to provide food to the flowers. These products comprise acidifiers and biocides and optionally sugars. These products are available from Pokon.

"gibberellic acid" is a plant-growth-promoting hormone, with a formula of $C_{19}H_{22}O_6$ and a CAS Registry Number of 77-06-5.

"gibberellins" are white, crystalline, optically active acids. They are a group of plant-growth regulators (hormones), isolated in 1938 and widely distributed in flowering plants that promotes elongation of shoots and coleoptiles.

"Nalco" refers to Nalco Chemical Company, One Nalco Center, Naperville, Ill., U.S.A., 60563, (630) 305-1000.

The instant claimed invention is a method to determine whether the desired amount of treatment product is present in water that cut flowers are placed in; comprising the steps of:

a) adding a known amount of an inert fluorescent tracer to a known amount of treatment product, with said treatment product being suitable for application to water that cut flowers are placed in;

b) applying said treatment product to water that cut flowers are placed in;

c) using a fluorometer to measure the fluorescent signal of said inert fluorescent tracer in said water that cut flowers are placed in; and optionally, d) adjusting the amount of treatment product applied to said water that cut flowers are placed in, based on the measured fluorescent signal of said inert fluorescent tracer.

Fluorescent tracers suitable for use in the method of the instant claimed invention are those inert fluorescent materials that have a fluorescent signal that can be measured using a fluorometer. All inert fluorescent tracer materials suitable for use in the method of the instant claimed invention must be selected such that their fluorescent signal is still detectable without masking of the signal by background fluorescence present in the flower water. Masking of the signal is defined as background fluorescence at the excitation wavelength greater than a 5% threshold with respect to the signal of the inert fluorescent tracer.

The meaning of the term "inert", as used herein is that an inert fluorescent tracer is not appreciably or significantly affected by any other chemistry in the treatment product or in said water that cut flowers are placed in, or by the other system parameters such as microbiological activity, biocide concentration, heat changes or overall heat content. To quantify what is meant by "not appreciably or significantly affected", this statement means that an inert fluorescent compound has no more than a 10% change in its fluorescent signal, under conditions normally encountered in cut flower water containing treatment product(s).

Suitable inert fluorescent tracer include, but are not limited to, 1,5-naphthalenedisulfonic acid disodium salt (1,5-NDSA),
2-amino-1-naphthalenesulfonic acid,
5-amino-2-naphthalenesulfonic acid,
4-amino-3-hydroxyl-1-naphthalenesulfonic acid,
6-amino-4-hydroxyl-2-naphthalenesulfonic acid,
7-amino-1,3-naphthalenedisulfonic acid, potassium salt,
4-amino-5-hydroxy-2,7-naphthalenedisulfonic acid,
5-dimethylamino-1-naphthalenesulfonic acid,
2,6-naphthalenedicarboxylic acid, dipotassium salt,
2-anthracenesulfonic acid, sodium salt, quinoline (CAS Registry No. 91-22-5),
1-ethylquinaldinium iodide,
dibenzofuransulfonic acid,
Brilliant Acid Yellow 8G (CAS Registry No. 2391-30-2, i.e. Lissamine Yellow FF, Acid Yellow 7),
cresyl violet acetate (CAS Registry No. 10510-54-0),
Safranine O (CAS Registry No. 477-73-6),
bathophenanthrolinedisulfonic acid disodium salt (CAS Registry No. 52746-49-3),
Titan Yellow (CAS Registry No. 1829-00-1, i.e. Thiazole Yellow G),
Celestine Blue (CAS Registry No. 1562-90-9),
Sandoz CW (CAS Registry No. 56509-06-9, i.e. Flu. Bright, 235),
Sandoz CD (CAS Registry No. 16470-24-9, i.e. Flu. Bright. 220),
Sandoz TH-40 (CAS Registry No. 32694-95-4),
Tinopal 5BM-GX (CAS Registry No. 169762-28-1),
Keyfluor White ST (CAS Registry No. 144470-48-4, i.e. Flu. Bright. 28),
Phorwite CL (CAS Registry No. 12270-53-0, i.e. Flu. Bright. 191),
Phorwite BKL (CAS Registry No. 61968-72-7, i.e. Flu. Bright. 200),
Leucophor BSB (CAS Registry No. 68444-86-0, i.e. Leucophor AP, Flu. Bright. 230),
Leucophor BMB (CAS Registry No. 16470-24-9, i.e. Leucophor U, Flu. Bright. 290),
Keyfluor White CN (CAS Registry No. 16470-24-9),
Tinopol DCS (CAS Registry No. 205265-33-4),
1-amino-4-naphthalene sulfonic acid,
1-amino-7-naphthalene sulfonic acid,
amino 2,5-benzene disulfonic acid,
1,3,6,8-pyrenetetrasulfonic acid, tetrasodium salt,
8-hydroxy-1,3,6-pyrenetrisulfonic acid, trisodium salt (i.e. Pyranine),
3,4,9,10-perylenetetracarboxylic acid,
bis-N-methylacridinium (i.e. Lucigenin),
2-(4-aminophenyl)-6-methylbenzothiazole,
fluorescein (CAS Registry No. 2321-07-5, i.e. Acid Yellow 73, Uranine),
Sulforhodamine B (CAS Registry No. 3520-42-1, i.e. Acid Red 52),
Rhodamine WT (CAS Registry No.37299-86-8),
Resazurin (CAS Registry No. 550-82-3),
Rhodalux (CAS Registry No. 550-82-3),
Anthrasol Green IB (CAS Registry No. 2538-84-3, i.e. Solubilized Vat Dye),
Acridine Orange (CAS Registry No. 65-61-2),
Phorwite BHC 766 (CAS Registry No. 52237-03-3),
Tinopal CBS-X (CAS Registry No. 27344-41-8),
Tinopal RBS 200,
Pylaklor White S-15A (CAS Registry No. 6416-68-8) and their ammonium, potassium and sodium salts.

The preferred inert fluorescent tracer is 1,3,6,8-pyrenetetrasulfonic acid, tetrasodium salt.

All of these inert fluorescent tracers are either available commercially from Nalco, or other companies, or can be synthesized using techniques known to people of ordinary skill in the art.

The selection of which inert fluorescent tracer to use, is based on matching the fluorescent tracer to the treatment product. The method used to select the optimum inert fluorescent tracer is to use a fluorometer to detect whatever fluorescent signals are present in cut flower water containing a specific treatment product. Then an inert fluorescent tracer is added to the treatment product and the fluorometer is used to detect its fluorescent signal in the water that the treatment product is placed in. If it is not possible to detect the fluorescent signal of the inert fluorescent tracer, due to background fluorescence, or interference from the fluorescent signal of the treatment product itself, then either more inert fluorescent tracer can be used, or an alternative inert fluorescent tracer can be selected for use with that treatment product. The alternative inert fluorescent tracer is selected such that its excitation and emission wavelengths are different than those of the background fluorescent signal(s) and the fluorescent signal of the treatment product. This method of selection of inert fluorescent tracer can be accomplished without undue experimentation.

When using the inert fluorescent tracer in treatment products for cut flowers, it is generally desirable to employ the least amount of inert fluorescent tracer that is practical for the circumstances. It is, of course, understood that the amount of the inert fluorescent tracer added to said water that cut flowers are placed in has to be at least an amount sufficient for the fluorescent signal measurements to be made. For practical purposes, the dosage of the fluorescent tracer in the water that the cut flowers are placed in, should be from about 50 parts per billion (hereinafter "ppb") to about 150 ppb, preferably about 100 ppb. In order to obtain this level of inert fluorescent tracer in the water that the cut flowers are placed in, the amount of inert fluorescent tracer added to the concentrated treatment product itself can be anywhere from about 100 to about 3000 times higher than this.

Of course, it is to be understood that it is possible to use greater amounts of inert fluorescent tracer. The upper limit of the amount of inert fluorescent tracer used is practically limited by economics, and not by performance.

The tracer is added to products that are added to the water used to keep cut flowers fresh. These products include, but are not limited to, treatment products applied to cut flower water in order to prevent leaf yellowing, treatment products applied to cut flower water in order to prevent vascular plugging of cut flower stems by bacteria, and optionally formulated to provide food to the flowers, treatment products applied to cut flower water in order to prevent ethylene damage, and treatment products applied to cut flower water in order to prevent leaf yellowing and/or extend vase life and/or reduce stem growth. Chemically speaking, these treatment products include gibberellins, gibberellic acid, aluminum sulfate and biocides, aluminum sulfate and surfactant, quaternary ammonium compounds, aminooxy-acetic acid, silver nitrate, sugars, acidifiers and biocides. These compositions are known to people of ordinary skill in the art. Cut flower water treatment products are available commercially, under various trade names, from Pokon.

Fluorometers suitable for use in the method of the instant claimed invention are commercially available. Suitable fluorometers include TRASAR® 350, TRASAR® 3000, TRASAR® 700 and TRASAR® 8000 fluorometers, all available from Nalco.

The fluorometers are set for the excitation and emission wavelength of the inert fluorescent tracer that is being used in the treatment product. For example, the fluorometer used should be set for an excitation wavelength of between about 360 nm and about 380 nm, preferably from about 365 nm to about 375 nm, and an emission wavelength of about 400 nm, in order to detect 1,3,6,8-pyrenetetrasulfonic acid, tetrasodium salt. Other settings are required for other inert fluorescent tracers. The "Emission Wavelengths" in this table represent the wavelength at or near the point at which a maximum fluorescent emission is obtained. For a listing of these other settings, please see the following table.

| Name | Excitation Wavelength $\lambda_{ex}$ (In nm) | Emission Wavelength $\lambda_{em}$ (In nm) |
|---|---|---|
| 1,5-naphthalenedisulfonic acid disodium salt (1,5-NDSA), | 289 | 328 |
| 2-amino-1-naphthalenesulfonic acid | 342 | 398 |
| 5-amino-2-naphthalenesulfonic acid | 330 | 468 |
| 4-amino-3-hydroxyl-1-naphthalenesulfonic acid | 346 | 444 |
| 6-amino-4-hydroxyl-2-naphthalenesulfonic acid | 306 | 406 |
| 7-amino-1,3-naphthalenedisulfonic acid | 353 | 446 |
| 4-amino-5-hydroxy-2,7-naphthalenedisulfonic acid | 356 | 418 |
| 5-dimethylamino-1-naphthalenesulfonic acid | 328 | 490 |
| 2,6-naphthalenedicarboxylic acid, dipotassium salt | 291 | 369 |
| 2-anthracenesulfonic acid, sodium salt | 361 | 416 |
| quinoline | 304 | 403 |
| 1-ethylquinaldinium iodide | 312 | 396 |
| Dibenzofuransulfonic acid | 287 | 317 |
| Brilliant Acid Yellow 8G | 417 | 509 |
| cresyl violet acetate | 586 | 613 |
| Safranine O | 518 | 567 |
| Bathophenanthrolinedisulfonic acid disodium salt | 283 | 396 |
| Titan Yellow | 340 | 422 |
| Celestine Blue | 342 | 420 |
| Sandoz CW | 337 | 428 |
| Sandoz CD | 333 | 428 |
| Sandoz TH-40 | 332 | 423 |
| Tinopal 5BM-GX | 369 | 434 |
| Keyfluor White ST | 358 | 428 |
| Phorwite CL | 339 | 426 |
| Phorwite BKL | 345 | 418 |
| Leucophor BSB | 336 | 430 |
| Leucophor BMB | 337 | 427 |
| Keyfluor White CN | 326 | 424 |
| Tinopol DCS | 332 | 436 |
| 1-amino-4-naphthalene sulfonic acid | 325 | 420 |
| 1-amino-7-naphthalene sulfonic acid | 310 | 380 |
| amino 2,5-benzene disulfonic acid | 310 | 380 |
| 8-hydroxy-1,3,6-pyrenetrisulfonic acid, trisodium salt (i.e. Pyranine) | 459 (pH 9.1) | 504 (pH 9.1) |
| 3,4,9,10-perylenetetracarboxylic acid | 463 | 477 |

-continued

| Name | Excitation Wavelength $\lambda_{ex}$ (In nm) | Emission Wavelength $\lambda_{em}$ (In nm) |
|---|---|---|
| bis-N-methylacridinium (i.e. Lucigenin) | 428 | 485 |
| 2-(4-aminophenyl)-6-methylbenzothiazole | 347 | 413 |
| Fluorescein | 488 | 509 |
| Sulforhodamine B | 562 | 577 |
| Rhodamine WT | 556 | 575 |
| Resazurin | 568 | 578 |
| Rhodalux | 518 | 567 |
| Anthrasol Green IB | 480 | 543 |
| Acridine Orange | 482 | 517 |
| Phorwite BHC 766 | 343 | 423 |
| Tinopal CBS-X | 354 | 427 |
| Tinopal RBS 200 | 363 | 451 |
| Pylaklor White S-15A | 353 | 425 |

It is known in the art of fluorescent tracer technology to relate the fluorescent signal of an inert fluorescent tracer to the amount of inert fluorescent tracer present. Then by knowing the amount of inert fluorescent tracer present, the amount of treatment product present can be calculated, because a known amount of an inert fluorescent tracer is always added to a known amount of the treatment product, thus making the proportional relationship between the inert fluorescent tracer and the treatment product also known.

By using the measured value of fluorescent signal of the inert fluorescent tracer, the amount of treatment product present can be known, and if desired, the amount of treatment product present, can then be adjusted, to the level required in order to ensure optimal flower quality. The level required is known to people of ordinary skill in the art of cut flower treatment products with the goal being the amount of treatment product present is selected such that optimal flower quality is obtained to provide flowers that can remain in saleable condition for as long as possible.

Changes can be made in the composition, operation and arrangement of the method of the present invention described herein without departing from the concept and scope of the invention as defined in the following claims.

What is claimed is:

1. A method to determine whether the desired amount of treatment product is present in water that cut flowers are placed in; comprising the steps of:
   a) adding a known amount of an inert fluorescent tracer to a known amount of a treatment product, with said treatment product being suitable for application to water that cut flowers are placed in;
   b) applying said treatment product to water that cut flowers are placed in;
   c) using a fluorometer to measure the fluorescent signal of said inert fluorescent tracer in said water that cut flowers are placed in;
   d) using the fluorescent signal of said inert fluorescent tracer to determine the amount of inert fluorescent tracer present in said water that cut flowers are placed in;
   e) correlating the amount of inert fluorescent tracer present in said water that cut flowers are placed in with the amount of treatment product present in said water that cut flowers are placed in;
   f) comparing the amount of treatment product present in said water that cut flowers are placed in with the desired amount of treatment product that is supposed to be present in said water that cut flowers are placed in; and optionally
   g) adjusting the amount of treatment product applied to said water that cut flowers are placed in, based on the measured fluorescent signal of said inert fluorescent tracer.

2. The method of claim 1 in which said inert fluorescent tracer is selected from the group consisting of 1,5-naphthalenedisulfonic acid disodium salt, 2-amino-1-naphthalenesulfonic acid, 5-amino-2-naphthalenesulfonic acid, 4-amino-3-hydroxyl-1-naphthalenesulfonic acid, 6-amino-4-hydroxyl-2-naphthalenesulfonic acid, 7-amino-1,3-naphthalenedisulfonic acid, potassium salt, 4-amino-5-hydroxy-2,7-naphthalenedisulfonic acid, 5-dimethylamino-1-naphthalenesulfonic acid, 2,6-naphthalenedicarboxylic acid, dipotassium salt, 2-anthracenesulfonic acid, sodium salt, quinoline, 1-ethylquinaldinium iodide, dibenzofuransulfonic acid, cresyl violet acetate, bathophenanthrolinedisulfonic acid disodium salt, 1-amino-4-naphthalene sulfonic acid, 1-amino-7-naphthalene sulfonic acid, amino 2,5-benzene disulfonic-acid, 1,3,6,8-pyrenetetrasulfonic acid, tetrasodium salt, 8-hydroxy-1,3,6-pyrenetrisulfonic acid, trisodium salt, 3,4,9,10-perylenetetracarboxylic acid, bis-N-methylacridinium, 2-(4-aminophenyl)-6-methylbenzothiazole, resazurin, fluorescein and their ammonium, potassium and sodium salts.

3. The method of claim 1 in which said inert fluorescent tracer is selected from the group consisting of an inert fluorescent tracer with CAS Registry No. 2391-30-2, an inert fluorescent tracer with CAS Registry No. 477-73-6, an inert fluorescent tracer with CAS Registry No. 1829-00-1, an inert fluorescent tracer with CAS Registry No. 1562-90-9, an inert fluorescent tracer with CAS Registry No. 56509-06-9, an inert fluorescent tracer with CAS Registry No. 16470-24-9, an inert fluorescent tracer with CAS Registry No. 32694-95-4, an inert fluorescent tracer with CAS Registry No. 169762-28-1, an inert fluorescent tracer with CAS Registry No. 144470-48-4, an inert fluorescent tracer with CAS Registry No. 12270-53-0, an inert fluorescent tracer with CAS Registry No. 12270-53-0, an inert fluorescent tracer with CAS Registry No. 61968-72-7, an inert fluorescent tracer with CAS Registry No. 68444-86-0, an inert fluorescent tracer with CAS Registry No. 205265-33-4, an inert fluorescent tracer with CAS Registry No. 37299-86-8, an inert fluorescent tracer with CAS Registry No. 2321-07-5, an inert fluorescent tracer with CAS Registry No. 550-82-3, an inert fluorescent tracer with CAS Registry No. 2538-84-3, an inert fluorescent tracer with CAS Registry No. 65-61-2, an inert fluorescent tracer with CAS Registry No. 52237-03-3, an inert fluorescent tracer with CAS Registry No. 27344-41-8, an inert fluorescent tracer with CAS Registry No. 6416-68-8 and the ammonium, potassium and sodium salts of said inert fluorescent tracer.

4. The method of claim 1 in which said inert fluorescent tracer is 1,3,6,8-pyrenetetrasulfonic acid, tetrasodium salt.

5. The method of claim 1 in which said treatment product is selected from the group consisting of treatment products applied to cut flower water in order to prevent leaf yellowing, treatment products applied to cut flower water in order to prevent vascular plugging of cut flower stems by bacteria and optionally formulated to provide food to the flowers, treatment products applied to cut flower water in order to prevent ethylene damage, and treatment products applied to cut flower water in order to prevent leaf yellowing and/or extend vase life and/or reduce stem growth.

6. The method of claim 1 in which said treatment products are selected from the group of treatment products comprising gibberellins, gibberellic acid, aluminum sulfate and biocides, aluminum sulfate and surfactant, quaternary ammonium, compounds, aminooxyacetic acid, silver nitrate, sugars, acidifiers and biocides.

* * * * *